(12) United States Patent
Kuntz

(10) Patent No.: US 6,437,221 B1
(45) Date of Patent: Aug. 20, 2002

(54) GENE PROMOTER SEQUENCES AND USES THEREOF

(75) Inventor: Marcel Kuntz, Grenoble Cedex (FR)

(73) Assignee: Syngenta Limited, Bracknell (GB)

( * ) Notice: Subject to any disclaimer, the term of this patent is extended or adjusted under 35 U.S.C. 154(b) by 0 days.

(21) Appl. No.: 09/486,581

(22) PCT Filed: Sep. 25, 1998

(86) PCT No.: PCT/GB98/02898

§ 371 (c)(1),
(2), (4) Date: Feb. 29, 2000

(87) PCT Pub. No.: WO99/16879

PCT Pub. Date: Apr. 8, 1999

(30) Foreign Application Priority Data

Sep. 26, 1997 (GB) .............................................. 9720481

(51) Int. Cl.[7] .......................... A01H 5/00; C12N 15/82; C12N 15/63; C12N 15/67; C07H 21/04
(52) U.S. Cl. .................... 800/287; 435/320.1; 435/419; 435/468; 536/24.1; 800/298
(58) Field of Search ............................... 435/320.1, 419, 435/468; 536/24.1; 800/278, 298, 287

(56) References Cited

PUBLICATIONS

Benfey et al, "The Cauliflower Mosaic Virus 35 S Promoter: Combinatorial Regulation of Transcription in Plants" Nov. 1990, Science vol. 250 pp. 959–966.*

Kim et al, "A 20 nucleotide upstream element is essential for the nopaline synthase (nos) promoter activity" 1994, Plant Molecular Biology vol. 24 pp. 105–117.*

Deruere et al, GenBank Accession No. X77290, Mar. 1995.*

* cited by examiner

Primary Examiner—Elizabeth F. McElwain
Assistant Examiner—Cynthia Collins
(74) Attorney, Agent, or Firm—Hale and Dorr LLP

(57) ABSTRACT

The promoters of the *Capsicum annuum* (bell pepper) fibrillin gene has the nucleotide sequence SEQ ID NO: 1. This promoter is useful for driving expression of foreign genes in transgenic plants.

5 Claims, 9 Drawing Sheets

GENE PROMOTER SEQUENCES AND USES THEREOF

Figure 1:
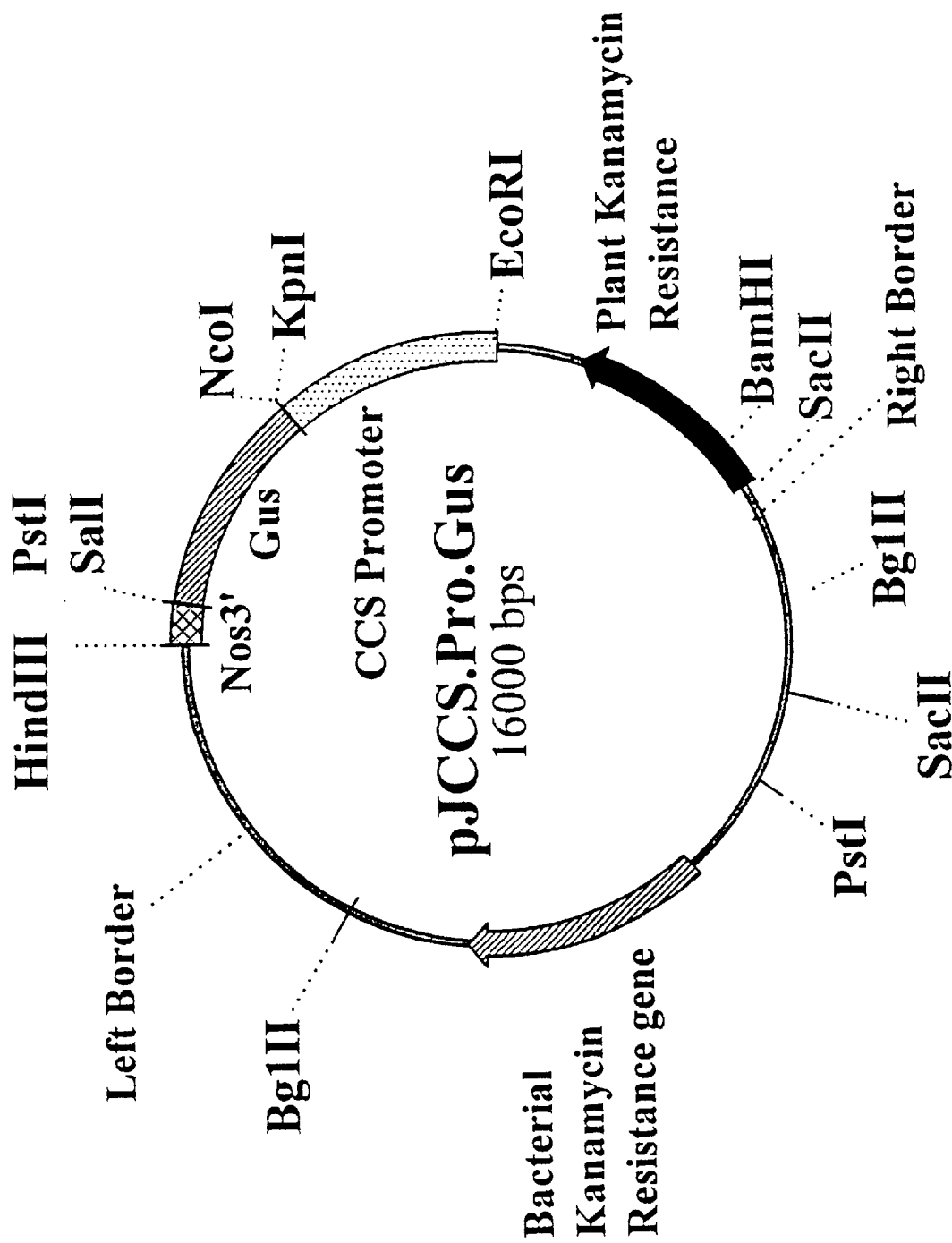

The present invention relates to gene promoter sequences isolated from bell pepper and their use to regulate chimeric gene expression in plants. In particular it describes the isolation and use of DNA sequences which permit a high level of expression of foreign genes in transgenic plants.

The expression of genes in plants is controlled by a number of regulatory components, including nucleic acid and protein elements. Where the plant gene exists as double stranded DNA, the primary steps of expression involve the production of a messenger RNA by a polymerase enzyme. The initiation of this part of the expression process is controlled by a region commonly referred to as the "promoter". The promoter lies upstream (5') of the protein encoding region and may be constitutive or tissue-specific, developmentally-regulated and/or inducible.

Within the promoter region there are several domains which are necessary for full function of the promoter. The first of these domains lies immediately upstream of the structural gene and forms the "core promoter region" containing consensus sequences, normally 70 base pairs immediately upstream of the gene. The core promoter region contains the characteristic CAAT and TATA boxes plus surrounding sequences, and represents a transcription initiation sequence which defines the transcription start point for the structural gene. The precise length of the core promoter region is indefinite but it is usually well-recognisable. Such a region is normally present, with some variation, in all promoters. The base sequences lying between the various well-characterised "boxes" appear to be of lesser importance.

The presence of the core promoter region defines a sequence as being a promoter: if the region is absent, the promoter is non-functional. Furthermore. the core promoter region is insufficient to provide full promoter activity. A series of regulatory sequences, usually upstream of the core, constitute the remainder of the promoter. The regulatory sequences determine expression level, the spatial and temporal pattern of expression and, for an important subset of promoters, expression under inductive conditions (regulation by external factors such as light, temperature, chemicals, hormones). Manipulation of crop plants to alter and/or improve phenotypic characteristics (such as productivity or quality) requires the expression of heterologous genes in plant tissues. Such genetic manipulation therefore relies on the availability of means to drive and to control gene expression as required; for example, on the availability and use of suitable promoters which are effective in plants and which regulate gene expression so as to give the desired effect(s) in the transgenic plant. It is advantageous to have the choice of a variety of different promoters so that the most suitable promoter may be selected for a particular gene, construct, lo cell, tissue, plant or environment.

Promoters (and other regulatory components) from bacteria, viruses, fungi and plants have been used to control gene expression in plant cells. Numerous plant transformation experiments using DNA constructs comprising various promoter sequences fused to various foreign genes (for example, bacterial marker genes) have led to the identification of useful promoter sequences. It has been demonstrated that sequences up to 500–1000 bases in most instances are sufficient to allow for the regulated expression of foreign genes. However, it has also been shown that sequences much longer than 1 kb may have useful features which permit high levels of gene expression in transgenic plants. A range of naturally-occurring promoters are known to be operative in plants and have been used to drive the expression of heterologous (both foreign and endogenous) genes in plants: for example, the constitutive 35S cauliflower mosaic virus promoter, the ripening-enhanced tomato polygalacturonase promoter (Bird et al, 1988, Plant Molecular Biology, 11:651–662), the E8 promoter (Diekman & Fischer, 1988, EMBO, 7:3315–3320) and the fruit specific 2A11 promoter (Pear et al, 1989, Plant Molecular Biology, 13:639–651) and many others.

As stated above, successful genetic manipulation relies on the availability of means to control plant gene expression as required. The scientist uses a suitable expression cassette (incorporating one or more promoters and other components) to regulate gene expression in the desired manner (for example, by enhancing or reducing expression in certain tissues or at certain developmental stages). The ability to choose a suitable promoter from a range of promoters having differing activity profiles is thus important.

In the present invention, we have isolated and fully sequenced the fibrillin gene promoter and the capsanthin-capsorubin synthase gene promoter from bell pepper (*Capsicum annuum*). The fibrillin promoter (FIB) essentially controls the production of the protein known as "fibrillin" in peppers. This fibrillin protein is associated with the plant chromoplasts and is involved in the packaging and organisation of carotenoids. It is the FIB promoter that regulates the accumulation of fibrillin during chromoplast differentiation.

The capsanthin-capsorubin synthase promoter (CCS) controls the production of the enzyme capsanthin-capsorubin synthase. This enzyme catalyses the conversion of the ubiquitous 5,6-epoxycarotenoids, antheraxanthin and violaxanthin, into capsanthin and capsorubin, respectively. It is the CCS promoter that specifically regulates the CCS gene during chloroplast to chromoplast differentiation.

The present invention aims to provide, inter alia, alternative promoters capable of driving gene expression in plants. We believe the present invention provides new developmentally regulated promoters which may be particularly useful in controlling chimeric gene expression in particular parts of a plant at a specific stage during development e.g. fruit ripening. This may be especially useful in plants such as tomato plants.

According to the present invention, there is provided a DNA sequence encoding a bell pepper fibrillin gene promoter capable of driving gene expression in plants having the sequence shown in SEQ ID NO 1 or active variants thereof.

Further according to the present invention, there is provided a DNA sequence encoding a bell pepper capsanthin-capsorubin gene promoter capable of driving gene expression in plants having the sequence shown in SEQ ID NO 2 or active variants thereof.

The cDNA sequence of the bell pepper FIB gene from the ATG initiation codon to a position 214 bp upstream, and of the CCS gene from the ATG initiation codon to a position 200 bp upstream have been previously described by Deruere et al (1994) (Biochem. Biophys. Res.Commnun. 199 (3) 1144–50). Similarly, the cDNA sequence of the CCS gene from the ATG initiation codon to a position 66 bp upstream has been described by Bouvier et al (The Plant Journal 6 (1) 45–54). The invention does not extend to these DNA sequences per se but does cover their use in the constructs, expression cassettes and the methods of the invention as described further herein.

"Active variants" are DNA sequences partially homologous to SEQ ID NO 1 or SEQ ID NO 2 which retain promoter activity. It may be possible to alter the level or type of activity of these promoters by manipulating their sequences: for example, by altering the nucleotide sequence in key regulatory regions, by truncating the sequence or by deleting parts within the sequence.

The promoters of the invention are suitable for incorporation into DNA constructs encoding any target gene or transcribable DNA region so that the target gene is expressed when the construct is transformed into a plant. The DNA construct preferably contains a transcription termination signal.

The bell pepper FIB and CCS promoters may be synthesised ab initio using the sequence shown in SEQ ID NO 1 and SEQ ID NO 2 as a guide. Alternatively, the promoters may be isolated from plant genomic DNA libraries using suitable probes derived from the said sequences or the promoter may be isolated using a PCR approach.

In practice the promoter of the invention may be inserted as a promoter sequence in a recombinant gene construct designed for use in a plant. The construct is then inserted into the plant by transformation. Any plant species may be transformed with the construct, and any suitable transformation method may be employed. It is preferred that plants to be transformed with the promoters according to the present invention are plants containing chromoplasts.

According to a second aspect of the invention, there is provided a plant gene expression assette comprising the bell pepper FIB or CCS promoter operatively linked to a target gene, the promoter having the sequence shown as SEQ ID No 1, SEQ ID No 2 or active variants hereof.

The target gene is a DNA sequence which may be derived from an endogenous plant gene or from a foreign gene of plant, fungal, algal, bacterial, viral or animal origin. Normally it is a sequence other than the sequence encoding the FIB or CCS protein which follows the FIB or CCS promoter in the naturally occuring bell pepper FIB or CCS gene. The target gene may be a single gene or a series of genes. The target gene is adapted to be transcribed into functional RNA under the action of plant cell enzymes such as RNA polymerase. Functional RNA is RNA which affects the biochemistry of the cell: for example, it may be mRNA which is translated into protein by ribosomes or it may be RNA which inhibits the translation of mRNA related to it. Thus the target gene sequence may be a sense sequence encoding at least part of a functional protein or an antisense sequence.

The expression cassette is suitable for general use in plants. In practice the DNA construct comprising the expression cassette of the invention is inserted into a plant by transformation. Any transformation method suitable for the target plant or plant cells may be employed, including infection by *Agrobacterium tumefaciens* containing recombinant Ti plasmids, electroporation, microinjection of cells and protoplasts, microprojectile transformation, pollen tube transformation and transformation of plant cells using mineral fibres (U.S. Pat. No. 5,302,523, International Patent Application Publication Number W094/28148). The transformed cells may then in suitable cases be regenerated into whole plants in which the new nuclear material is stably incorporated into the genome. Both transformed monocotyledonous and dicotyledonous plants may be obtained in this way. Transgenic plant technology is for example described in the following publications: Swain WF, 1991, TIBTECH 9: 107–109; Ma JKC et al, 1994, Eur J Immunology 24: 131–138; Hiatt A et al, 1992, FEBS Letters 307:71–75; Hein MB et al 1991, Biotechnology Progress 7: 455–461; Duering K, 1990, Plant Molecular Biology 15: 281–294.

Examples of genetically modified plants which may be produced include but are not limited to field crops, cereals, fruit and vegetables such as: canola, sunflower, tobacco, sugarbeet, cotton, soya, maize, wheat, barley, rice, sorghum, mangoes, peaches, apples, pears, strawberries, bananas, melons, tomatoes, potatoes and carrot.

The invention further provides a plant cell containing a gene expression cassette according to the invention. The gene expression cassette may be stably incorporated in the plant's genome by transformation. The invention also provides a plant tissue or a plant comprising such cells, and plants or seeds derived therefrom.

The invention further provides a method for controlling plant gene expression comprising transforming a plant cell with a plant gene expression cassette having a bell pepper FIB or CCS promoter operatively linked to a target gene, whereby the activated promoter drives expression of the target gene. The promoter may be activated under certain spatial, temporal, developmental and/or environmental conditions.

In order to determine their temporal and spatial expression, the promoter fragments of the bell pepper FIB and CCS genes are fussed to the GUS (β-glucuronidase) reporter gene in DNA constructs suitable for plant transformation. GUS accumulation in transgenic plants may then be monitored.

β-glucuronidase is a bacterial enzyme which catalyses the conversion of 5-Methylumbelliferyl glucuronide (MUG) to 4-Methylumbelliferone (MU) and Glucuronic acid. The conversion is measured by way of a fluorometer at 365 nm excitation 455 emission. A time course of the reaction can be carried out allowing the conversion rate to be measured in nanoMoles MU formed/mg protein/minute. This activity allows the analysis of gene expression controlled by the promoter in the transformed plants.

The invention will now be described by way of example and with reference to the following figures of which;

FIG. 1: Is a diagrammatic map of plasmid pJCCS.Pro.Gus.

Figure 2:
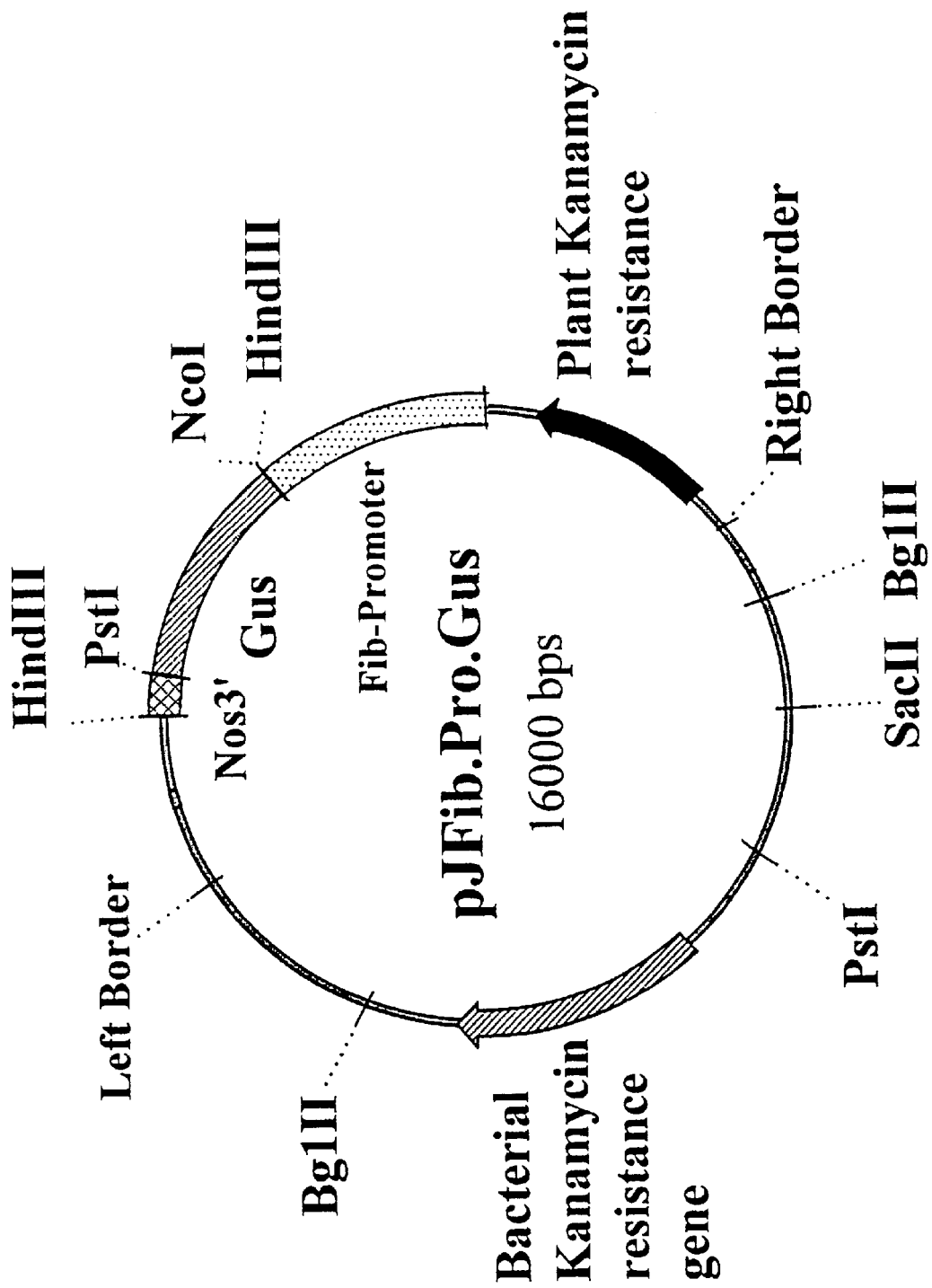

FIG. 2: Is a diagrammatic map of plasmid pJFIB.Pro.Gus.

Figure 3:
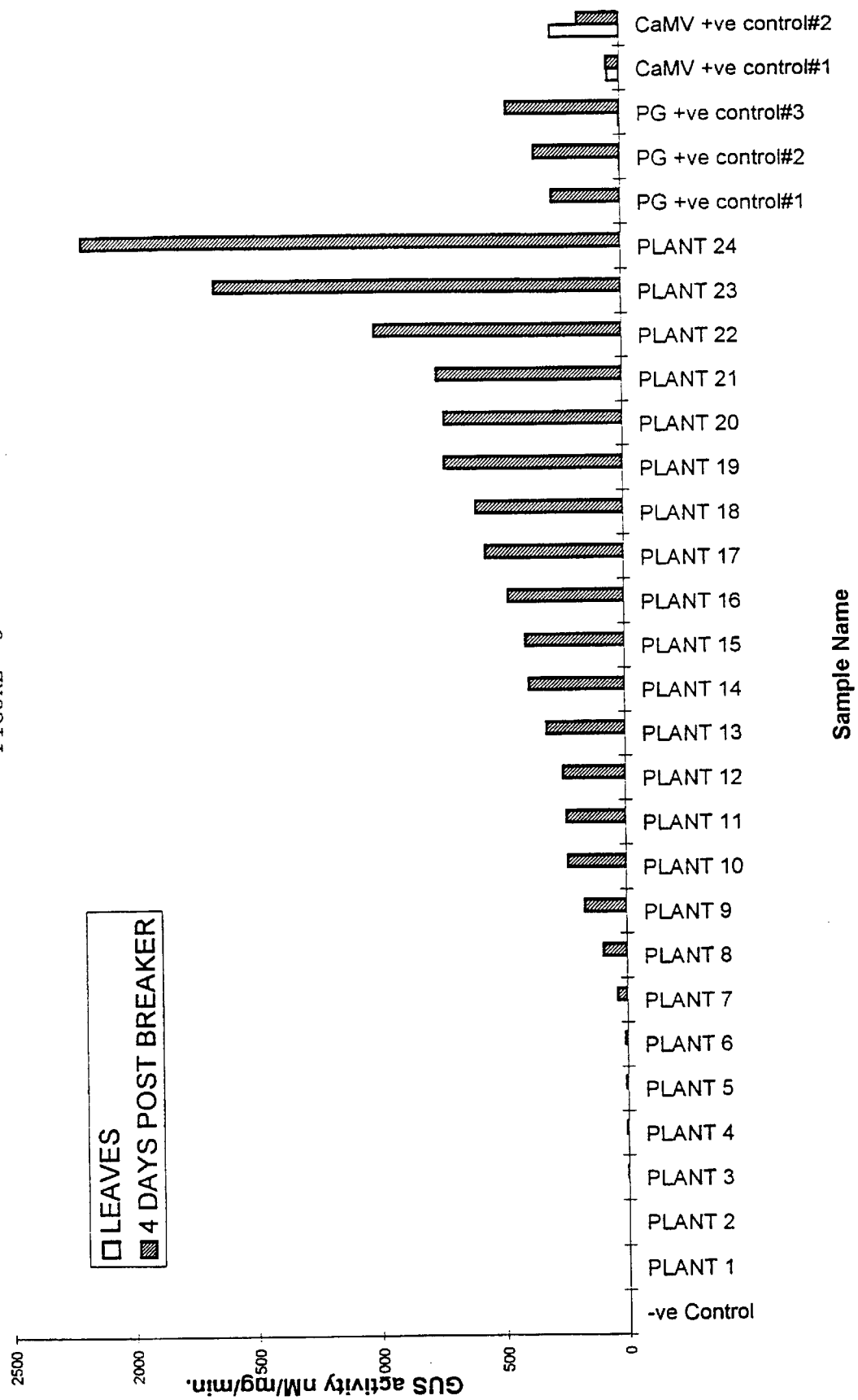

FIG. 3: Graph representing the levels of GUS activity in plants transformed with construct 1.

Figure 4:
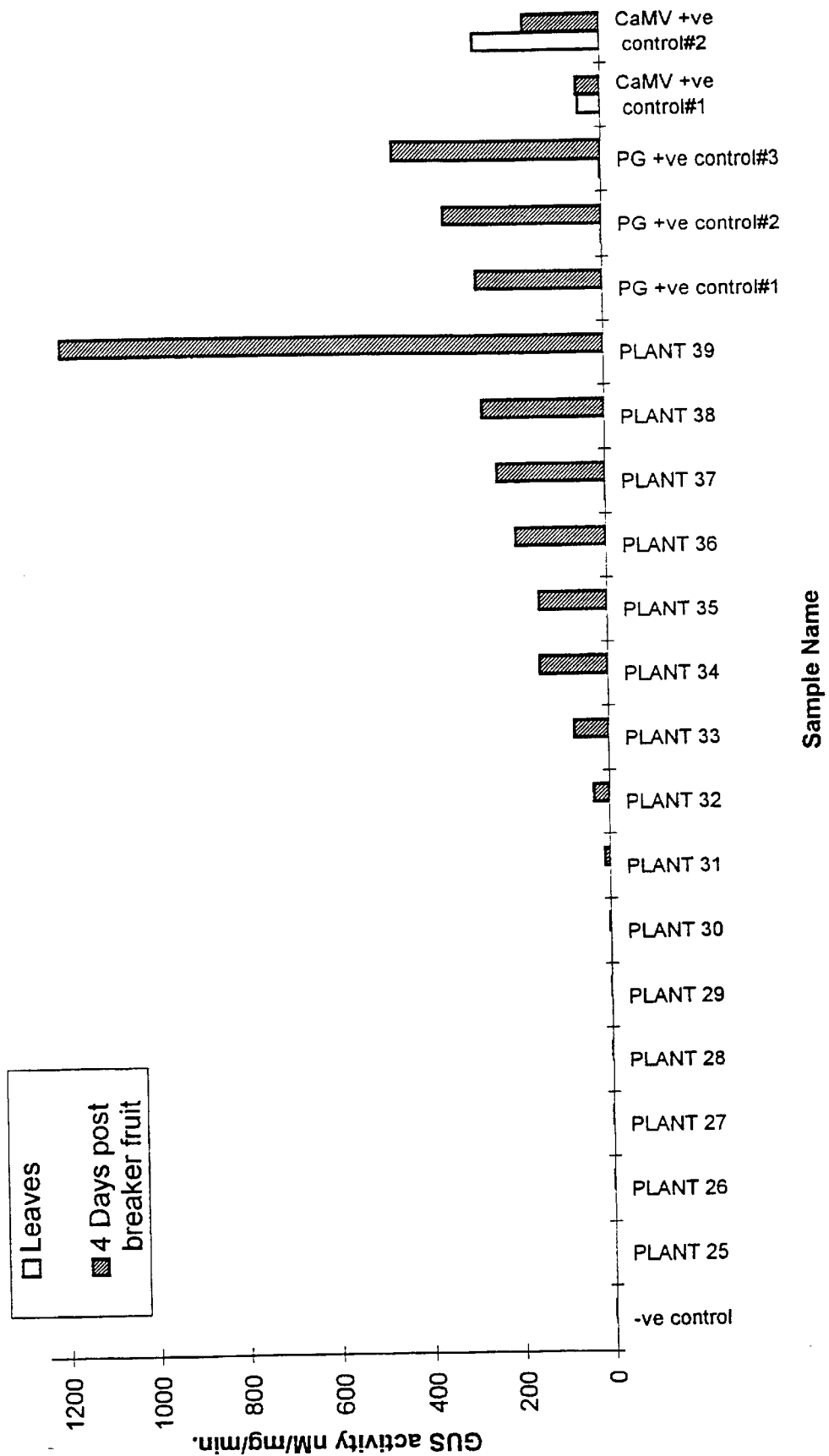

FIG. 4: Graph representing the levels of GUS activity in plants transformed with construct 2.

Figure 5:
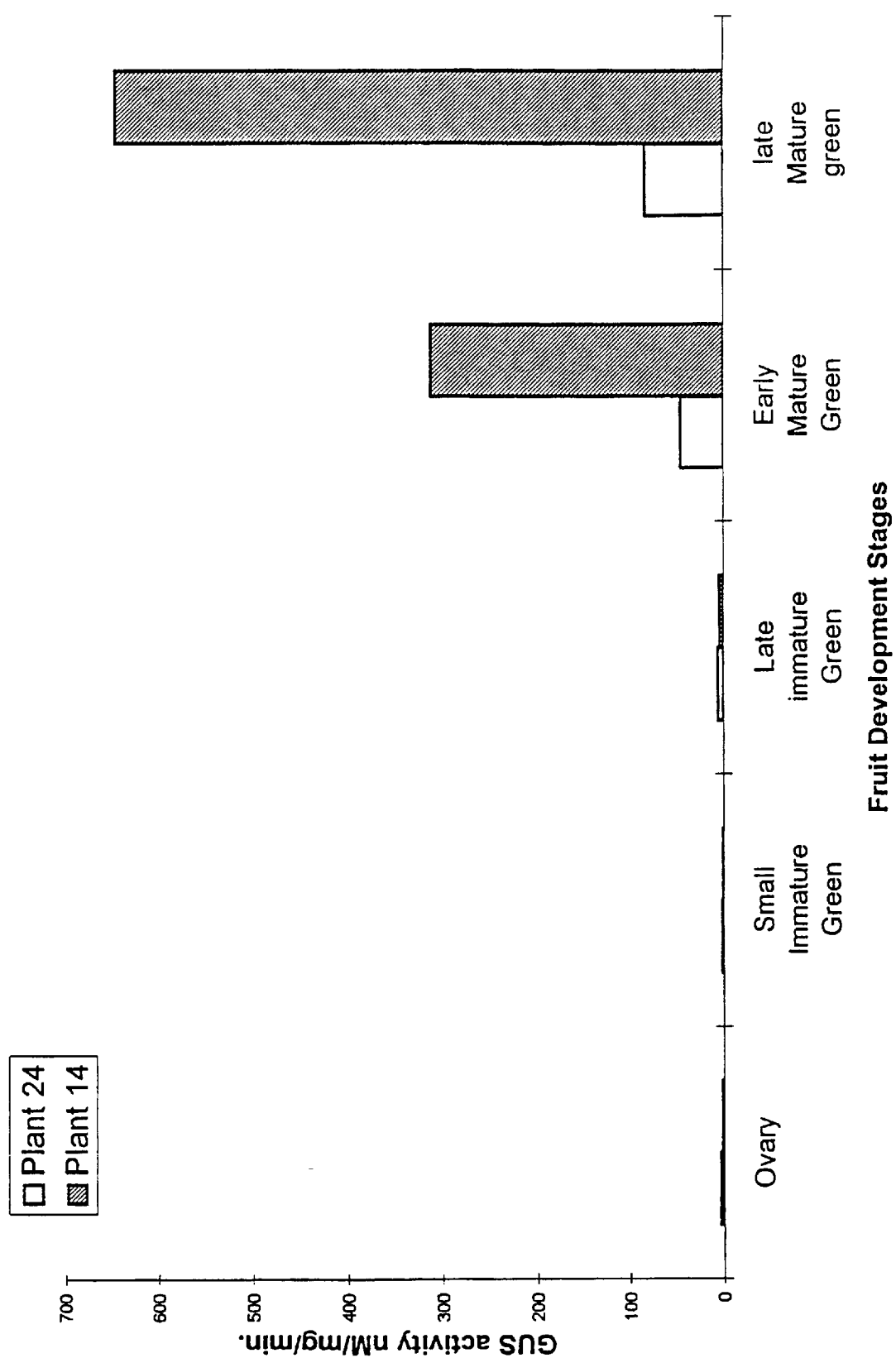

FIG. 5: Graph representing the fruit development results in plants transformed with construct 1.

Figure 6:
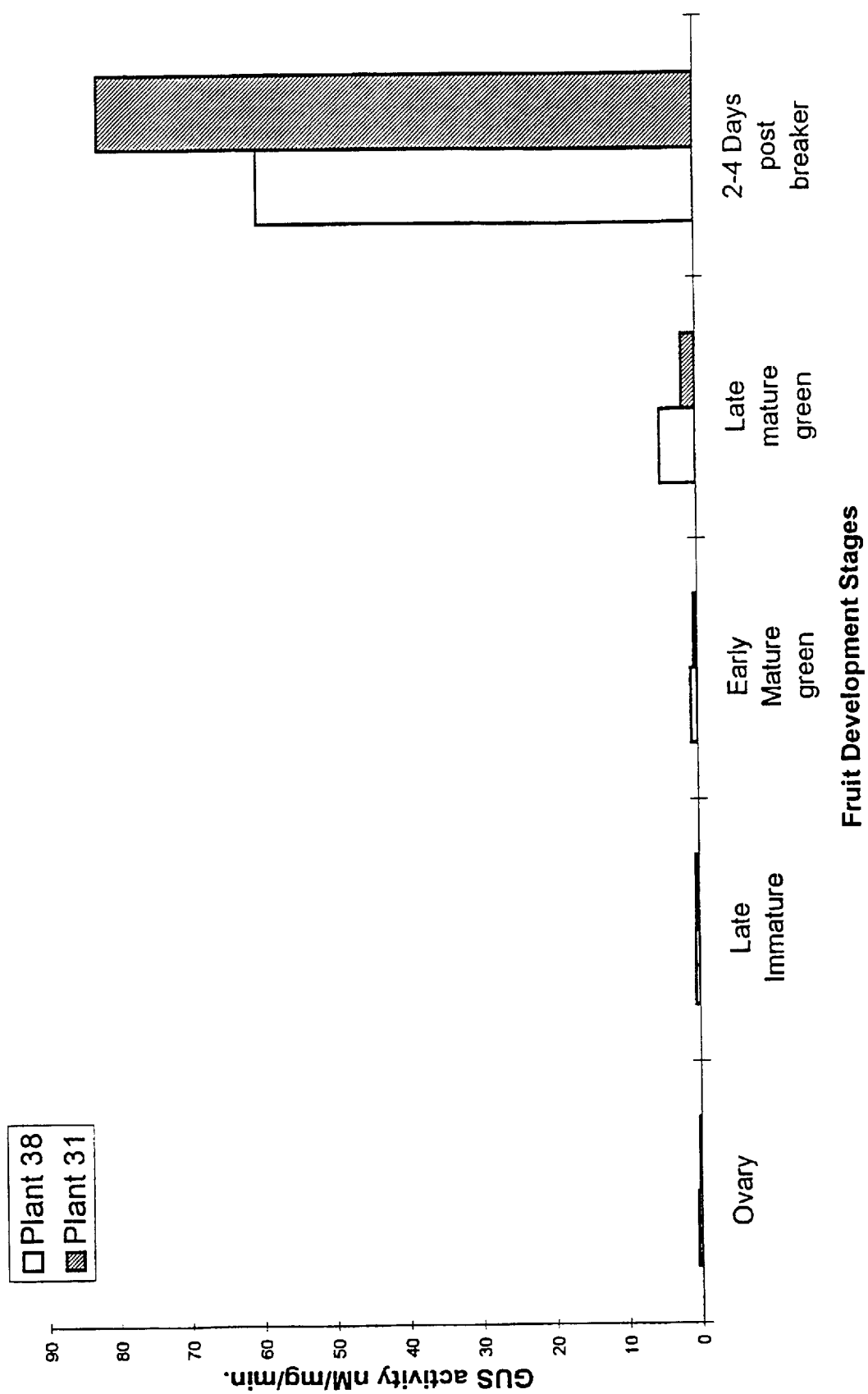

FIG. 6: Graph representing the fruit development results in plants transformed with construct 2.

Figure 7:
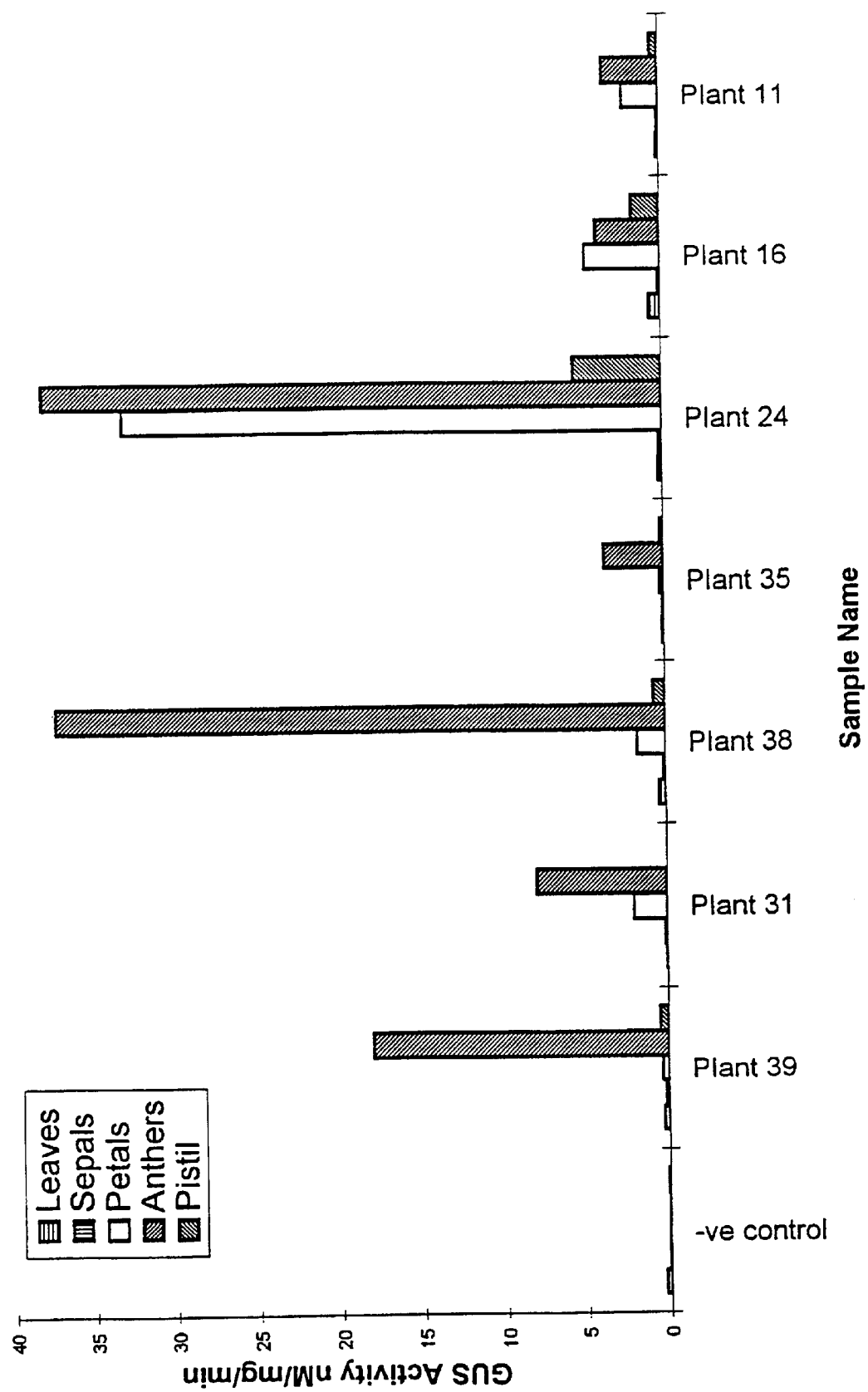

FIG. 7: Graph representing the results obtained from floral organs of plants transformed with constructs 1 and 2.

Figure 8:
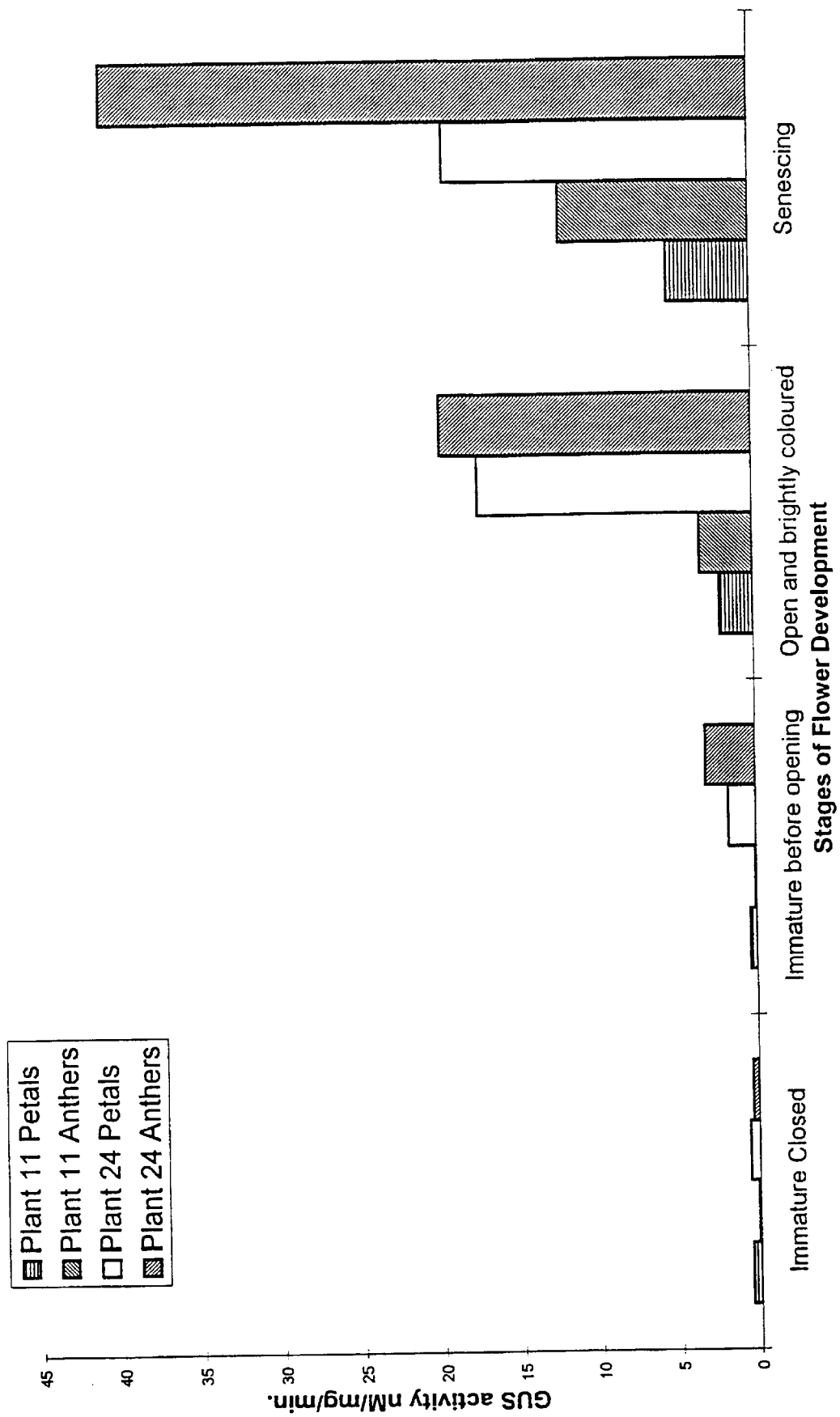

FIG. 8: Graph representing the levels of GUS activity in developing flowers in plants 15 transformed with construct 1.

Figure 9:
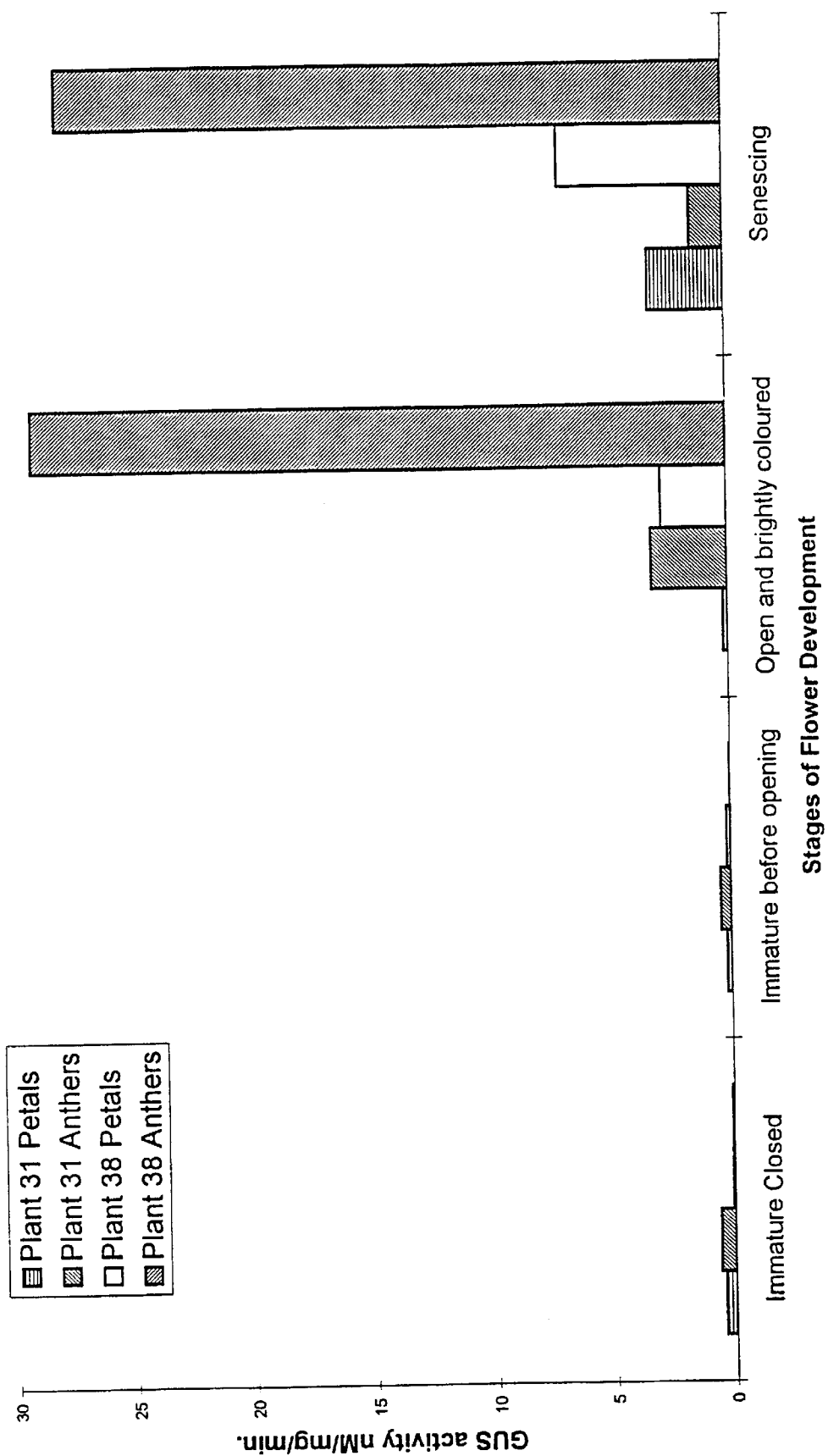

FIG. 9: Graph representing the levels of GUS activity in developing flowers in plants transformed with construct 2.

EXAMPLE 1

Isolation of the sequences from the cDNA's.

A pepper genomic fragment (Deruere et al. 1994, Biochem. Biophys Res. Commun. 199 (3) 1144–50)) was characterised by hybridisation to the pepper cDNA for fibrillin (Deruere et al. 1994, The Plant Cell 6 119–33) and by sequence analysis. A 1784 bp fragment upstream of the coding region was further characterised by sequence analysis. This promoter sequence is shown here as SEQ ID No 1. Nucleotides 1782 to 1784 in SEQ ID No. 1 correspond to the ATG start codon of the GUS gene.

Similarly, a pepper genomic fragment (Deruere et al. 1994, Biochem. Biophys. Res. Commun. 199 (3) 1144–50) was characterised using the CCS cDNA (Bouvier et al. 1994, The Plant Journal 6 (1) 45–54 paper) and a 2312 bp fragment containing the putative promoter was sequenced and is shown here as SEQ ID No 2. Nucleotides 2310 to 2312 in SEQ ID No 2 correspond to the ATG start codon of the GUS gene. Unlike SEQ ID No 1, SEQ ID No 2 is mainly composed of multiple direct repeats.

EXAMPLE 2

SEQ ID No 1 and SEQ ID No 2 were site-directed mutagenised in order to introduce a coI restriction site at the position of the translation initiation codon (ccATGg). This col restriction site and a distal restriction site were used to insert SEQ ID No 1 and SEQ ID No 2, respectively, in front of the GUS gene subcdoned in the plasmid pBluescriptKS and previously modified by site directed mutagenesis in order to introduce a NcoI restriction site at the position of the initiation codon. In addition, the nos terminator sequence had been previously inserted downstream of the GUS gene.

These constructs were termed pFib.Pro.Gus (construct 1) and pCCS.Pro.Gus (construct 2), respectively. The whole gene fusion consisting of the putative promoter region fused to the GUS gene and nos terminator were ligated in the plant expression vector JR1Ri to produce pJFib.Pro.Gus and pJCCS.Pro.Gus, respectively.

EXAMPLE 3

Transformation and regeneration of Tomato Explants Transformation was performed with the vectors pJFib.Pro-.Gus and pJCCS.Pro.Gus. These plasmids were transferred to *Agrobacterium tumefaciens* LBA 4404 (a microorganism widely available in plant biotechnology) and used to transform tomato stem explants. The transformations produced two separate plant lines of primary transformants containing either the pJFib.Pro.Gus construct or the pJCCS.Pro.Gus construct. The transformation of tomato stem segments was carried out according to standard protocols (e.g. Bird et al. (1988), *Plant Mol. Biol.* 11, 651–662). Transformed plants were selected on antibiotic (kanamycin) containing growth media.

EXAMPLE 4

Approximately 50 primary transformants were produced (approximately 25 lines containing the pJFib.Pro.Gus or construct 1 and 25 lines containing the pJCCS.Pro.Gus construct). The presence of the transgenes was detected by PCR analysis and Southern blot analysis. PCR positive plants showed 1–3 inserted copies and occasionally up to 7 inserted copies. Plants were analysed for GUS activity in young leaves and in 4 day-post breaker ripening fruits (TABLE 1 and 2) using a fluorimetric assay (Jefferson RA: Plant Mol. Biol. Rep. 5: 387405. 1987). No direct correlation between transgene copy number and GUS activity was found. Only background GUS activity could be detected in leaves, while high GUS activity was found in ripening fruits.

Plants containing single insertion were used for fisher analysis. GUS activity significantly higher than in leaves was also detected in various flower organs such as petals, anthers and pistil (style and stigma, ovary) and at developmental stages characterised by chromoplast formation (yellow pigmentation). Low GUS activity was detected in fruit pericarp from immature fruits and Gus activity was found to increase at an early mature green stage for FIB and at a late mature green stage for CCS immediately before visible sign of ripening were visible). Gus activity continued to increase during further ripening. Histochemical assay for GUS activity showed significant GUS activity in anthers of both FIB and CCS plants, as well as in petals for FIB plants (confirming that the CCS promoter is more active in anthers than in petals, while the FIB promoter is equally active in anthers and petals). Histochemical assays also showed that both promoters are active in various fruit tissues (pericarp, columella, locular tissue).

The following tables show the data obtained from the analysis of the primary transformants. All the data in the following tables are a measurement of the GUS activity in nano Moles MU formed per milligram protein per minute (nM/mg/min).

TABLE 1

Illustrates the GUS activity of tomato leaves and 4 days post "breaker" fruit from plants transformed with construct 1. The table also includes a transformation control (negative control) and a series of positive controls including plants transformed with the CaMV-GUS and Polygalacturonase-GUS constructs. The "breaker" stage in tomato fruit ripening is an intermediate between the mature green and fully ripe stages.

TABLE 1

| PLANT NAME | LEAVES | FRUIT. 4 DAYS POST BREAKER. |
|---|---|---|
| Transformation Control | 0.27 | 0.80 |
| PLANT 1 | 0.06 | 0.37 |
| PLANT 2 | 0.18 | 0.5 |
| PLANT 3 | 0.082 | 1.7 |
| PLANT 4 | 0.38 | 6.4 |
| PLANT 5 | 0.15 | 7.8 |
| PLANT 6 | 0.094 | 10 |
| PLANT 7 | 0.13 | 40 |
| PLANT 8 | 0.11 | 97 |
| PLANT 9 | 0.3 | 170 |
| PLANT 10 | 0.087 | 237 |
| PLANT 11 | 0.18 | 240 |
| PLANT 12 | 0.125 | 255 |
| PLANT 13 | 0.49 | 320 |
| PLANT 14 | 0.18 | 390 |
| PLANT 15 | 0.31 | 400 |
| PLANT 16 | 0.68 | 470 |
| PLANT 17 | 0.34 | 560 |
| PLANT 18 | 0.3 | 600 |
| PLANT 19 | 0.6 | 720 |
| PLANT 20 | 0.13 | 720 |
| PLANT 21 | 0.15 | 750 |
| PLANT 22 | 0.14 | 1000 |
| PLANT 23 | 0.32 | 1650 |
| PLANT 24 | 0.26 | 2200 |
| PG + ve#1 | 0.1 | 280 |
| PG + ve#2 | 1.2 | 350 |
| PG + ve#3 | 3.6 | 460 |
| CaMV + ve#1 | 50 | 54 |
| CaMV + ve#2 | 280 | 170 |

These data clearly show that the fibrillin promoter is providing high expression levels of GUS in the fruit of plants 9 through 24 and little or no expression in the leaves. In particular the expression levels in the fruit of plants 16 to 24 are higher than that of the positive controls which contain the fruit specific PG promoter. As expected the constitutive CaMV 35S promoter shows high levels of expression of GUS in both the fruit and leaves providing further evidence that the Fibrillin promoter is not constitutively expressing throughout the plant.

TABLE 2

Shows the GUS activity in the leaves and 4 days post breaker fruit of plants transformed with construct 2.

| PLANT NAME | LEAVES | FRUIT. 4 DAYS POST BREAKER |
|---|---|---|
| NEGATIVE CONTROL | 0.27 | 0.80 |
| PLANT 25 | 0.1 | 0.5 |
| PLANT 26 | 0.12 | 0.94 |
| PLANT 27 | 0.12 | 1 |
| PLANT 28 | 0.075 | 1.1 |
| PLANT 29 | 0.17 | 1.5 |
| PLANT 30 | 0.1 | 3.3 |
| PLANT 31 | 0.018 | 12.5 |
| PLANT 32 | 0.081 | 34.5 |
| PLANT 33 | 0.033 | 76 |
| PLANT 34 | 0.32 | 150 |
| PLANT 35 | 0.12 | 150 |
| PLANT 36 | 0.38 | 200 |
| PLANT 37 | 1.1 | 240 |
| PLANT 38 | 0.4 | 270 |
| PLANT 39 | 0.3 | 1200 |
| PG + ve#1 | 0.1 | 280 |
| PG + ve#2 | 1.2 | 350 |
| PG + ve#3 | 3.6 | 460 |
| CaMV + ve#1 | 50 | 54 |
| CaMV + ve#2 | 280 | 170 |

These data also indicate that the expression levels of GUS are high in the post breaker fruit and very low in the leaves. Plants 34 to 38 show high levels of expression comparable to that of the fruit specific promoter controls, and plant 39 shows extremely high levels of expression.

Results from Tables 1 and 2 clearly show high levels of GUS expression in the ripening fruit for plants transformed with the FIB and CCS promoters respectively. These data provide good evidence that these promoters are strong and possibly ripening induced.

TABLE 3

Shows the results of the fruit development of two plants transformed with construct 1. The fruit were analysed for GUS activity a varying stages of development up to and including the mature green stage.

| PLANT NAME | OVARY | SMALL IMMA-TURE | LATE IMMA-TURE | EARLY MATURE GREEN | LATE MATURE GREEN |
|---|---|---|---|---|---|
| PLANT 24 | 3.4 | 1.9 | 6.2 | 45 | 83 |
| PLANT 14 | 1.9 | 0.38 | 4.4 | 312 | 646 |

The aim of this experiment was to determine at what stage the FIB promoter was induced. Results indicate that GUS expression is at quite low levels until the late immature green stage and then begins to rise markedly at the early mature green stage. Further increase during fruit ripening is less pronounced from one fruit to another.

TABLE 4

Shows the results of GUS expression levels during the fruit development stages of two plants transformed with construct 2. This experiment includes analysis at the post breaker stage.

| PLANT NAME | OVARY | LATE IMMA-TURE | EARLY MATURE GREEN | LATE MATURE GREEN | 2 to 4 DAYS POST BREAKER |
|---|---|---|---|---|---|
| PLANT 38 | 0.54 | 0.56 | 0.98 | 5 | 60 |
| PLANT 31 | 0.27 | 0.5 | 0.48 | 2 | 82 |

The CCS promoter also appears to increase expression around the mature green/breaker fruit ripening stages. It appears that the FIB promoter produces the strongest expression levels and begins expressing at the early mature green ripening stage, whereas the CCS promoter expression levels are lower and rise around the breaker ripening stage.

TABLE 5

Shows the results obtained from the floral organs from plants transformed with construct 1 and construct 2. This experiment was designed to test the expression levels in the flowers as they also contain areas of chromoplast differentiation which are connected with the activity of these promoters. The GUS expression levels were assayed in the different parts of the tomato flower, providing the data as set out below.

| PLANT NAME | CONSTRUCT NUMBER | LEAVES | SE-PALS | PET-ALS | AN-THERS | PISTIL |
|---|---|---|---|---|---|---|
| NEGATIVE CONTROL | 2 | 0.27 | 0.041 | 0.077 | 0.036 | 0.09 |
| PLANT 39 | 2 | 0.3 | 0.16 | 0.38 | 18 | 0.51 |
| PLANT 31 | 2 | 0.018 | 0.15 | 2 | 8 | No Data |
| PLANT 38 | 2 | 0.4 | 0.135 | 1.7 | 37.3 | 0.73 |
| PLANT 35 | 2 | 0.12 | 0.08 | 0.26 | 3.6 | 0.22 |
| PLANT 24 | 1 | 0.26 | 0.22 | 33 | 38 | 5.4 |
| PLANT 16 | 1 | 0.68 | 0.128 | 4.6 | 3.9 | 1.7 |
| PLANT 11 | 1 | 0.18 | 0.1 | 2.2 | 3.4 | 0.5 |

These results show that expression levels with the CCS promoter are higher in the petals, pistils and in particular the anthers when compared with the leaves and sepals. This is also true for the FIB promoter, however these plants appear to have higher expression in the petals and pistils, when compared with the plants containing the CCS promoter.

TABLE 6

Experiments were conducted on the developing tomato flowers and GUS expression levels were calculated at the different stages of flowering. The first assays being when the immature flower is closed, also when the immature flower is elongating just before opening, when the mature flower is completely open and brightly coloured and finally when the flower is senescing.

| PLANT NAME | IMMATURE (CLOSED) | IMMATURE BEFORE (OPENING) | OPEN AND BRIGHTLY COLOURED | SENESCING |
|---|---|---|---|---|
| PLANT 11 Petals | 0.51 | 0.43 | 2.15 | 5.25 |
| PLANT 11 Anthers | 0.11 | 0.0925 | 3.4 | 12 |
| PLANT 24 Petals | 0.6 | 1.75 | 17.4 | 19.3 |
| PLANT 24 Anthers | 0.39 | 3.2 | 19.7 | 40.7 |

The data show that the promoter activity increases with the maturity of the flowers. This provides further evidence that the FIB promoter is developmentally controlled showing a large rise in promoter activity at the flower maturity stage.

TABLE 7

Using the same criteria as Table 6, these results show the GUS activity of the petals and the anthers of developing flowers in plants transformed with construct 2.

TABLE 7

| PLANT NAME | IMMATURE (CLOSED) | IMMATURE (BEFORE) (OPENING) | OPEN AND BRIGHTLY COLOURED | SENESCING |
|---|---|---|---|---|
| PLANT 31 Petals | 0.41 | 0.195 | 0.195 | 3.2 |
| PLANT 31 Anthers | 0.6 | 0.44 | 3.2 | 1.4 |
| PLANT 38 Petals | 0.077 | 0.175 | 2.75 | 6.95 |
| PLANT 38 Anthers | 0.065 | 0.03 | 29.1 | 27.9 |

The data provide further evidence that the CCS promoter is developmentally controlled showing a large rise in promoter activity around the flower maturity stage.

TABLE 8

This table shows the effects of environmental stress on the expression levels in the leaves. This experiment was designed to test the effect of promoter activity when environmental stresses are placed upon the plant. The GUS assays were conducted on tomato leaves transformed with either construct 1 or 2, that had been treated in the following ways; detached leaf placed in water, detached leaf dehydrated and wounded leaf.

TABLE 8

| PLANT NAME | YOUNG LEAF CONTROL | YOUNG LEAF DETACHED AND PLACED IN WATER | YOUNG LEAF DETACHED AND DEHYDRATED | YOUNG LEAF WOUNDED | OLD LEAF CONTROL | OLD LEAF DETACHED AND PLACED IN WATER | OLD LEAF DETACHED AND DEHYDRATED | OLD LEAF WOUNDED |
|---|---|---|---|---|---|---|---|---|
| Plant 13 | 0.08 | 0.097 | 0.58 | 0.1 | 0.19 | 0.2 | 1.1 | 0.19 |
| Plant 14 | 0.027 | 0.049 | 0.13 | 0.083 | | | | |
| Plant 24 | 0.26 | 0.75 | 2.9 | 0.075 | | | | |
| Plant 16 | 0.2 | 0.11 | 0.38 | 0.093 | | | | |
| Plant 39 | 0.066 | 0.068 | 0.068 | 0.055 | | | | |
| Plant 38 | 0.086 | 0.11 | 0.092 | 0.145 | | | | |

These data provide evidence that the FIB promoter can be slightly induced by environmental stress such as water defecit but to a much lower level than that observed during fruit ripening or flower development.

What is claimed is:

1. A DNA sequence encoding a Capsicum anuum fibrillin gene promoter capable of driving gene expression in plants, wherein the DNA sequence comprising the sequence shown in SEQ ID NO: 1.

2. A DNA construct comprising a promoter as claimed in claim 1 operatively linked to a transcribable DNA region and a transcription termination signal.

3. A transgenic plant, seed or any other form of regenerant having stably incorporated within its genome a DNA construct as claimed in claim 2.

4. A plant according to claim 3 in which the said plant is a tomato plant.

5. A method for controlling gene expression in a plant comprising transforming a plant cell with a plan gene expression cassette having a promoter as claimed in claim 1 operatively linked to a target gene.

* * * * *

SEQUENCE LISTING

<160> NUMBER OF SEQ ID NOS: 2

<210> SEQ ID NO 1
<211> LENGTH: 1784
<212> TYPE: DNA
<213> ORGANISM: Capsicum annuum

<400> SEQUENCE: 1
gataaatgat cgtattgact tagagtatac tggttaaaat tattatatat ctaataattt        60

```
atttgatgtt tagtaataa actaccatac tgttatttt attttaaact tactgtgaaa      120
gagagaatgc acttcagaaa actaaatatc tattacacat catctgaaat ggtcgtgagt      180
gaaccttttt gaatatataa tttaagttgc aaatagagtt atttgaagaa aaaaaaaaag      240
gaaaaagaaa cagtataatg ctccttgtc ctctagccca ccaaaaaagg aacaaatatt      300
aatttaatta gaaaaaaaca accttgagcg ggtcgaatta gtaggtcttt ccacattcaa      360
attactaatt ttaaaaatta ttgactactt caagattctt taatctttt tcctttgtat      420 tgagagagtc atcaaaaagc tcactcggga cgtgaaaaaa aatttgactt gctaattata      480
tctatattta ctaggtaaaa tcctaatctt attatcacat tatcactggg atttttcggc      540
attattctag ctaaatatct tgtgcaattc atgtcctcca ccacaaaaaa aatgcctaat      600
tttacaactt ttttggtatg aaagagagt aagaaaaag gaataagaga agtctgattg      660
aaagaaataa ggaggatga ataaaaaac aaagaaaat tctactagaa tttgtatgcc      720
gttggatgtg aatggaaacc aattttttg tctctcttgt tgttcaatt ttaaatttcc      780 gccaaacaga cacaaaatga tccttaactc cgctttacaa gcgatagtta cgtgtcttcc      840
tctctctccc ttgttgacgt atcttaaaaa ctccaaacta cccctggatt tttctaatct      900
ttaattaagg attatatata tatatatata tatatatata tatatatata tatatatata      960
tattatgata attaataatt aaatatttgc acatttaaaa gtctatttgg attgacttat     1020
tttagatgtt ttaaagttaa aataacttt aataatttt agtattcgaa taaactaaga     1080
aaggtgctta taagcacttt atgcctttac actacaatgt aaaaattaag tcaaaagtta     1140
ttaaacgaac ttattagtca aaagttaaag cgaatccaca caagcgctac gcttaatatt     1200
tttttagcca aagcgaatcc aaacaagcgc tacgtcaata ttcttttcct tttctttaat     1260
tgaaccatca atcctagatc tcactttctc tgacatggga cctaacatta acaatatgag     1320
ttgtggtgtg ataattcgag attccttcaa ccctaatagg aagtgctata gtgaaaaatg     1380
agccctccaa tatccgcatt caaatttaat ccgactttaa tgtagataca atgtgggaac     1440
cgatgggaaa gaacaaaagt aataagatat acaatatgtt ttcacacata gtgagatcta     1500
gaaagggtag atagtatgcc gttggtatct ctatcttaga ggtaaagtag aaaagttgtt     1560
tccaatcgat ccgaactcaa gagaaaaaca gtttagccga tgggaaataa agaaaagaaa     1620 aactaatttta ggagggtata tatgtctttg cacaaaggct aacctaaagc cctggctcgt     1680
ataaaacgcg atcattacag gattgcaaca taaacactca ttcaatcgaa gcttccctgt     1740
taatattatc attttgttcc ttctttattc actcttaaac catg                      1784
```

<210> SEQ ID NO 2
<211> LENGTH: 2312
<212> TYPE: DNA
<213> ORGANISM: Capsicum annuum

<400> SEQUENCE: 2

```
gaattcttcc aacagttcgt ttttagttt ctgttttggg aagaggagta ctacaaggta       60
ggacctccaa caatcaacaa tatctaagtt gcaaaagttt tgtgcgtttt tttagtttct      120
gtttcgagaa gaggaatact acaagttcgt ttttagttt ctgttttggg aagaggagta      180
ctgcaaggta ggacctccaa caattatcaa tatctaaatt gcaaaaattt cagttcgttt      240
ttagtttctg tttcgggaaa aggaatacta caagttcgtt tttagtttc tattttggga      300 agaggagtac tacaaggtag gacctccaat acctaaattg caaaaatttc agttcgtttt      360
```

```
ttagtttcag tttagggaag aggaatacta ctaggtagga cctccaacaa tcatcaatcc        420
agggttgcaa aaatttcagt tcgttttta gtttatgttt gggaagaaga atactacaag        480
gcagtggtgg agctacctta tgattagggg gttcatccga acctccttcg acggaaaatt       540
atactatttt tataagtgaa aattattttt tatgtatata taattgatgt tgaaccccct       600
tcggttagtt catgtatcta tatttttta ttttgaaccc cgatgaaaat ttgggctccg        660
ccactgctac aaggtaggac ctccaacaat caccaatacc taaattgcaa aaatttcagt      720
ttgctttta gtttctgttt tgggaagagg aatactacaa ggtaggacct ccaacaatca       780
ccaataccta aattgcaacg gttttttagt ttctgttttg ggaagaggaa tactacatgg      840
tagggcctcc aacaatcacc aatacctaaa ttgcaaaaat ttcagttcgt attttcgttt     900
ctattttggg aagtggaata gtataaggta ggacctccaa caatcaccaa tacctaaatt    960
gcaaaagttc cgattcattt tttagtttct gttttggaaa gagaaatact acaaggtagg  1020
gcctacaaca atcaccagta cctaaattgt aaaaatttca gttcgttttt tagtttctat   1080
tttgagaaga ggaatgctac aaggtagggc ctacaacaat caccagtacc taaattgtaa  1140
aaatttcagt tcgttttta gtttctgttt tgggaagagg aatactacaa ggtagggcct    1200
ccaacaatca gcaataccta aattacaaaa atttcaattc gtttttagt ttctgttttg   1260
ggaagaggaa tactacaagg cagtggcgga gctaccttat gattaggggt tcatccgaac  1320
ctccttcgac ggaaaattat actatttg tatagtaaaa attatttttt atgtatatat    1380
aattgatgtt gaacccctt cggttagttt gtgtatctat atttttttat tttgaacctc   1440
cttgataaaa aattttgact ccgccattgc tacaaggtag aacctccaac aatcaccaat  1500
acctaaattg caaaaatttc agttcgtttt ttaatttctg ttttgggaag aggaatacta  1560
caggcctcca acaatcacca atacctaaat tgcaaaattt tagtttgttt tttagtttct  1620
gttttgggaa gaggaatact acaaggtaag gcctccaaca atcaccaata cctaaattgc  1680
aaaaatttca gttcgtattt tcgtttctat tttgggaagt ggaatagtat aaggtaggac  1740
ctccaacaat caccaatacc taaattgcaa aagttccgat tcatttttta gtttctgttt  1800
tggaaagaga aatactacaa ggtagggcct ccaacaatca ccagtaccta aattgtaaaa  1860
atttcagttc gttttttagt ttctattttg ggaagtggaa tagtataagg taggacctcc  1920
aacaatcacc aatacctaaa ttgcaaaagt tccgattctt tttttagttt ctgttttgga  1980
aagagaaata ctacaagata ggaccttcaa caatcaccaa tacctaaatt gcaaaaactt  2040
cagttcattt tttagtttct gttttgggaa gaagaatact tcaaggtaac aatcaccaat  2100
acctaaatta aaaatttcag ttagtttttt agtttctgtt tttgggaaga ggaatacttt  2160
cttttgctat ataaagccaa agtaggtacc tataagcatc aatattttgt attgcttagt  2220
gattcccta gttcggtatt tcattttttt tcactatact atatcacctc ctctcataaa   2280
tagccattat aaatcttgca ttttctctaa tg                                 2312
```